US008756250B2

(12) United States Patent
Unger et al.

(10) Patent No.: US 8,756,250 B2
(45) Date of Patent: Jun. 17, 2014

(54) CLIENT MANAGEMENT SYSTEM

(75) Inventors: Paul Unger, Meridian, ID (US); Brian R. Ernesto, Meridian, ID (US); Rem L. Fox, Caldwell, ID (US)

(73) Assignee: Conex MPS, Inc., Meridian, ID (US)

( * ) Notice: Subject to any disclaimer, the term of this patent is extended or adjusted under 35 U.S.C. 154(b) by 382 days.

(21) Appl. No.: 12/800,676

(22) Filed: May 20, 2010

(65) Prior Publication Data

US 2011/0119307 A1    May 19, 2011

Related U.S. Application Data

(60) Provisional application No. 61/216,941, filed on May 22, 2009.

(51) Int. Cl.
*G06F 7/00* (2006.01)
*G06F 17/30* (2006.01)

(52) U.S. Cl.
USPC ................................ 707/783; 705/3; 707/941

(58) Field of Classification Search
USPC ....................... 707/783, 941; 705/3
See application file for complete search history.

(56) References Cited

U.S. PATENT DOCUMENTS

| 7,464,043 | B1 * | 12/2008 | Dussia | 705/3 |
|---|---|---|---|---|
| 7,509,264 | B2 * | 3/2009 | Hasan et al. | 705/3 |
| 7,640,271 | B2 * | 12/2009 | Logan, Jr. | 1/1 |
| 7,912,733 | B2 * | 3/2011 | Clements et al. | 705/2 |
| 7,953,609 | B2 * | 5/2011 | Zak et al. | 705/2 |
| 8,010,717 | B2 * | 8/2011 | Evans et al. | 710/16 |
| 8,332,466 | B1 * | 12/2012 | Cha et al. | 709/203 |
| 2003/0036683 | A1 * | 2/2003 | Kehr et al. | 600/300 |
| 2005/0165627 | A1 * | 7/2005 | Fotsch et al. | 705/3 |
| 2006/0004609 | A1 * | 1/2006 | Kenneth et al. | 705/3 |
| 2009/0024417 | A1 * | 1/2009 | Marks et al. | 705/3 |
| 2009/0099871 | A1 * | 4/2009 | Gadodia | 705/3 |
| 2009/0132284 | A1 * | 5/2009 | Fey et al. | 705/3 |
| 2009/0234916 | A1 * | 9/2009 | Cosentino et al. | 709/203 |
| 2010/0082372 | A1 | 4/2010 | Wen et al. | |
| 2010/0138232 | A1 * | 6/2010 | Ryan et al. | 705/2 |
| 2010/0153287 | A1 * | 6/2010 | Holzberg | 705/319 |
| 2010/0299155 | A1 * | 11/2010 | Findlay et al. | 705/3 |
| 2011/0082794 | A1 * | 4/2011 | Blechman | 705/50 |
| 2011/0161107 | A1 * | 6/2011 | Goldberg et al. | 705/3 |

OTHER PUBLICATIONS

Relay Health, Website Materials from www.relayhealth.com, Aug. 30, 2010.
Myca Health, Inc., Website Materials from www.hellohealth.com, Aug. 30, 2010.
Myca Health, Inc., Website Materials from www.closebyclinic.com, Aug. 30, 2010.
Myca Health, Inc., Website Materials from www.myca.com, Aug. 30, 2010.

* cited by examiner

*Primary Examiner* — Jeffrey A Burke
(74) *Attorney, Agent, or Firm* — Parsons Behle & Latimer (57) ABSTRACT

This invention relates to permission based collaborative health record system. Specifically, it relates to systems of and methods for creating authorized health records that care givers and patients can use to document their diagnoses, symptoms, outcomes, instructions and participation in the effort toward wellness.

11 Claims, 8 Drawing Sheets

CLIENT MANAGEMENT SYSTEM

CROSS REFERENCE TO RELATED APPLICATIONS

This application claims the benefit of U.S. provisional application no. 61/216,941 filed on May 22, 2009 entitled "Client Management System". The entirety of this application is hereby incorporated by reference.

BACKGROUND

To achieve better treatment outcomes, healthcare service providers are continually striving to improve the accuracy of diagnosis and the quality of treatment. Unfortunately, in the course of a traditional caregiver and patient relationship, poor communication, poor documentation and poor instruction (or the inability to correctly recall the instructions) inhibits the accuracy and efficacy of the diagnosis and the treatment plans. For example, data is typically entered into a health record by a nurse or credentialed professional who takes notes during the physical engagements based upon conversations with the patient. This requires the patient to recall from memory all the symptoms and issues that make up the related patient illness, a difficult task if some of the symptoms were not recurring or occurred sometime prior to the caregiver visit. The care giver then has to determine the best course of action and treatment plan based upon this data. Physically returning for caregiver visits during the treatment plan and follow up telephone calls are the only methods of communication to alter the course of action, note any challenges with treatment, change medications, and document all of this change process accurately. This leads to a higher cost of healthcare and longer patient durations toward improvement. Accordingly, an improved method of communication, documentation and instruction between patient and caregiver is desirable.

SUMMARY OF THE INVENTION

The following presents a brief summary of the innovation in order to provide a basic understanding of the aspects of the innovation. This summary is not an extended overview and is not intended to cover each and every element of the innovation or to limit its scope. A more detailed description is presented later.

The innovation disclosed and claimed herein is a centralized chronological record system and methods that allow one or multiple care givers and patients to participate in the treatment process by completing documentation in the form of notes, messages, audio, video, documents, and instructional assignments interactively. Accordingly, it overcomes the limitations of the traditional methods of communication, diagnosis, treatment and instruction by, for instance, permitting real time entry of symptoms into the health record, providing accurate, readily accessible and preserved treatment instructions, and dispensing of the time lag typically associated with the onset of a symptom or issue and a caregiver visit. Access to the record system is permitted through a secure authorization process using individualized credentials through a web browser. Particular tools embodied within the software enable the entry of time stamped documentation in to the central record system at anytime through a web browser regardless of location. Particular illustrations are described in connection with the following descriptions and the annexed drawings. These illustrations are indicative, however, of but a few of the various ways in which the principles of the innovation can be employed. Other advantages will be readily apparent from the detailed description that follows. The subject innovation is intended to include all aspects and equivalents.

DETAILED DESCRIPTION

The following information will describe the innovation in detail with reference to the drawings and numerals. The purpose of the following information is to establish a thorough understanding of the subject innovation. It may be obvious, that the innovation can be practiced without these specific details in other instances.

The dynamic creation of a permission based collaborative chronological health record is the key feature of the innovation. As further described herein, the innovation enables caregivers and patients to create collaboration tools including, but not limited to, notes, messages, audio files, video files, documents, and assignments with discrete permissions of read only, read/write, and no access through an asynchronous method. The record system allows caregivers and patients to facilitate complete participation in the health record and present the data in a threaded fashion through a permission based collaboration feature that is, in one embodiment, based on unique user IDs recognized by the system.

The target audience for this innovation are healthcare professionals that need to communicate with patients regarding, for example, care plans, illnesses, or ailments or for the purpose of education or collaboration. It should be understood that patient participation in readily accessible communication and record keeping is crucial in understanding patient results and administering a successful care plan. The system allows the logical flow and storing of communications so that historical data inputted by any party participating in the system. This, in turn, improves outcomes, safety, and satisfaction levels. Another advantage of maintaining the patient inputted data in the system is the reliable and accurate gathering of clinical research information due to actual patient documentation in the care plan. For example, a health record that includes note taking by the patient is likely to more effectively and readily document the poor side effects of a treatment plan than caregiver entered notes because in the case of patient entered notes, the note taker is directly affected. Such communications also allows prompt alteration of and more accurate administration of treatment actions.

Although described in regard to the patient-caregiver relationship, it should be recognized that workers or professionals in many different disciplines could use the system. Indeed, the system can be used in any discipline or profession in which information or common purposes and objectives are to be shared or exchanged to enhance the quality and delivery of the engagement.

A simple example of this operation can be explained by the following scenario: Caregiver 1 creates an account for their patient. The account builds a database of tables as selected by the caregiver equaling the number of collaboration features in the system with a logical binding to caregiver 1. Essentially what has occurred is a marriage between the caregiver and the patient database tables so that asynchronous data entries can be collected and presented to one another for communication and review if permitted by a security process controlled by both caregiver and patient. Further, the primary caregiver can add additional caregivers to the patient by request, thus joining multiple micro-database tables to the patient allowing multi-caregiver participation to the threaded asynchronous data. Any data entered can also be tagged with identifying information such as date, time or owner. The result is a multi-user joint record system that is date, time, owner identified, and threaded by chronological order per database table accessible and contributable by authorization.

Figure 1:
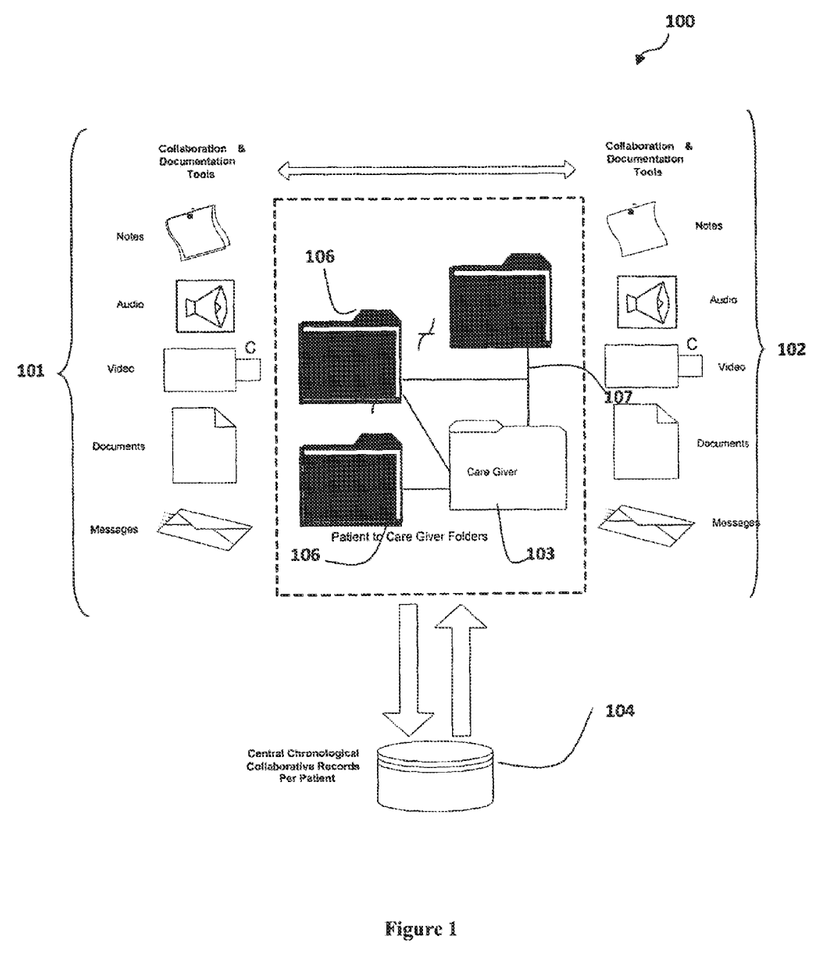
FIG. 1. Illustrates an example wire frame diagram of a system that facilitates collaborative record operations.

Depicted in FIG. 1 is a basic diagram of part of the system 100 that facilitates data exchange between patients and caregivers through various collaboration and documentation tools 101, 102 that reside on the system. Various patient collaboration tools 101 and caregiver collaboration tools 102 are shown. Independent entries can be made to any of the collaboration tools 101, 102 that are then stored and reconciled in the master folders and tables 103 and the record database 104. Each caregiver and patient is assigned a master folder 103 in the system that contains the collaboration and documentation tools 101, 102 to which the user has access. The system is a multi-tenant system where a master account folder 103 can create client account folders 106 and as this process is executed, logical bindings 107 are made for each client account folder 106 to interact with the master folder 103 automatically. The master account folder 103 can assign activities to one client folder 103 or many. So the automated relationship of the folder structure is one to one or one to many. The folders are permission based so each client log in has a unique folder 106 bound to the master folder 103. This creates the marriage of the client to professional folder relationship. It is secure and private by unique log in and password dynamically created. This function exists for each master folder account and has no limitations for quantity. The operational framework ties the user interface to their specific data sets stored within the record database. This is the execution framework allowing a button to call up a collaboration tool and related data table for the activity chosen. The system can use standard protocols with no special algorithms or search indices.

The collaboration and documentation tools 101, 102 may include, but are not limited to, a calendar, notes, a photo manager, an audio player, a goal manager, a motivation tool, an assignments tool, messaging and a video player.

The system may be designed to have a calendaring application. In one version of the calendar, the calendar includes all client appointment entries tied to the client account. So if a user clicks on the appointment on their calendar related to a specific client, the relevant client account is connected and fully presented for working an appointment. This is a transparency feature so the user does not have to look up a client appointment and then go find the client folder. It should be recognized that any date, deadline or appointment related data can be incorporated into the calendaring tool.

The system may be designed to have a notes application that resides on either the client or master accounts, or both.

Master notes are not visible to clients for purposes of specific information by choice. Client account notes are visible to master accounts used as reminders of discussion items for appointments and other action items. The notes application is bound to the security roles assigned by account creation and maintained by the data owner's authorization settings.

The system may be designed to have an application to store client photographs or other relevant images per client account. The uses for this can vary but any image can be selected and stored as the folder overlay for client display. The image can be displayed on the client folder and on the upper application frame for visual identification.

The system may be designed to have an audio application to record and playback voice based media between the client and master accounts. This allows voice based notes, and conversational questions and answers to be maintained in the system per account relationships.

The system may be designed to have a goal setting application. The goal setting application can be bound to the assignments application. In one embodiment, each master account has the ability to set multiple goals and award a point value to each goal. The goals may be presented in a progress chart at the top of the primary application frame as assigned client work is completed. One example of a workflow formula may be: Goal=points/assignment completion=% of yield for progress completion of a give task. The formula creates a visual representation of the workflow.

The system also may be designed to have a motivate application allowing milestone motivators to set encouragement for the clients to reach certain goals and objectives. Motivators are choice driven and can be any type of award item itemized in the application.

The system may be designed to have an assignments application that creates assignments for clients coupled to related goals. Assignments are choice driven and can range, for example, from watching a video, reading a document, getting information or sending a document. Each assignment presented to a client has a "mark complete" function that relates to progress on the assignment and this triggers the goal formula and progress bar presentation. The workflow formula is noted below: Assignment Complete=points earned/% of progress completed=visual progress chart.

The system may be designed to have a type based messaging system to communicate email like messages between the client and master accounts. The chronology and history of all conversations within this application are tied to historical record and accordingly not deleted. The messages are a common application other than the binding to chronology record keeping and related account communications. The basis is private interaction between the accounts within the system which is far more secure and reliable than email.

In addition, the system may be designed to have a video player that is used by master accounts to assign training, education, and related subject matter presentations to clients as assignments. The video application may have a text based foot note window used for describing key points in the video. It also contains a window for assignment number and due date targeted for completion. The mark complete function button on the video player executes the progress bar outlined in the assignments section above.

It should be understood that the foregoing are only examples of the collaboration and documentation tools that can be used in the system and professionals utilizing the system can add additional features or tools unique to the patient and the course of treatment. As described later, various options are available at account set up. In other words, each professional can choose their profile by discipline and populate the application with relevant tools required in the treatment program. The application will build dynamically by these choices. The client can make adjustments to their account anytime over the course of customer tenancy.

Figure 2:
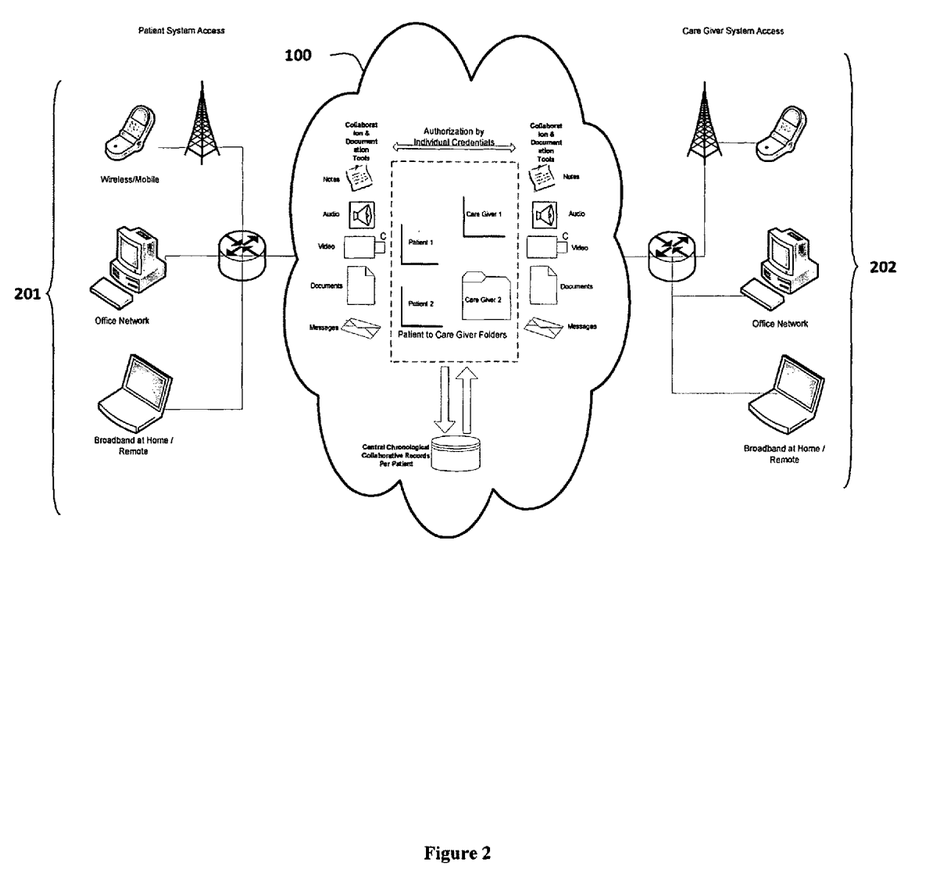
FIG. 2. Illustrates the networking and computing operation as it pertains to the innovation.

Referring now to FIG. 2, there is depicted system 200 which illustrates the access of the user to the system. It is to be understood that the system can be accessed and present data in multiple formats by way of any network connection (wired or wireless) through devices 201, 202 such as laptop or desktop computers, personal digital assistants (PDAs), cell phones, smart phones, or the like. Generally, the system includes a user interface (UI), which will be displayed on the user operated device 201, 202, and a record database 203. It should be understood that the entire system can be delivered through a web browser in the cloud computing system or the data could reside on a central server that is accessed remotely. Thus, any device that can provide an internet connection can be used as a device to access the user interface, with resulting access to the record database. In a contemplated embodiment, no software will be required to use the system other than a web browser.

The following usage scenarios will provide perspective to the functionality of the innovation. It is not intended to limit the scope of the innovation but to provide context as to the operational value. In these scenarios the caregiver is generally communicating to the client on an asynchronous basis through the collaboration tools over the Internet with a web browser in virtually any location where network access is available. The following is a common scenario:

A family has just seen a pediatrician that has diagnosed their child with autism. The parents are faced with a long term child learning disability that will involve many care providers to optimize the best for the child's outcome. The pediatrician will be involved in preparing the family with as much educational material and treatment planning as possible. The pediatrician opens a web browser and logs in to the system and creates the family account. The pediatrician assigns learning content based upon the diagnosis and enters notes regarding the diagnosis and treatment plan. The pediatrician also messages for the family to set up an appointment with a speech therapist. This data has been tracked in the chronological record. When the family arrives home their email has a notification that their account with the pediatrician is available. The family opens a web browser and logs in to the system and reviews the assignments and messages which then make an entry in to the chronological record and notify the pediatrician the tasks were completed. The pediatrician now has confirmation of the family progress on the course of action and invites the chosen speech therapist to the families account with permission to share notes with the pediatrician only. The family receives a notification to accept or deny account access with the speech therapist via email. The family logs in and chooses to accept. Their account displays a visual indicator showing the shared account and lists the two care givers they are working with. The speech therapist also is notified of the account invitation via email. The speech therapist now can open a web browser and log in to the system and see the new family account. The speech therapist can review the pediatrician notes and also assign specific learning content and message the family with regards to the first appointment and course of action based upon the diagnosis. These actions are entered in to the chronological history. The family is notified via email of the speech therapist assignments and messages and can log in to the system to review. This process is continued such that all information on current activity and progress can be checked anytime by the family, the speech therapist, and the pediatrician on a continual basis.

In an alternative scenario a physician sees a patient and determines the diagnosis is an auto-immune disorder. The physician wants to set a treatment plan that will administer a specific medication that has risk of side effects. The physician opens a web browser and logs in to the system and sets up the patient account. The physician assigns learning content of the related diagnosis and messages the treatment plan for the medication. The physician also enters related notes on the patient, diagnosis, and treatment plan. The patient picks up the medication from the pharmacy on the way home and begins the first treatment step that afternoon by taking the prescribed medication. The patient arrives home and reviews the email notification of the account readiness. The patient logs in to the system and reviews the learning assignments and messages. Upon completion the physician is notified of the patient task completion. The next day the patient has experienced some strange events that are believed to be side effects of the medication. The patient logs in to the system and messages the physician of the effects with a video displaying a visual effect. The physician is notified via the system of the patient update. The physician opens a web browser and logs in to the system to review the patient update. After review of the patient video, the physician determines a new course of treatment with a different medication. The physician messages the patient of the change with new instructions. Through the notifications, the patient logs in to the system and reviews the physician recommended changes later that day. The patient messages the physician a thank you message and can begin an altered treatment that evening. All of this asynchronous communication has been captured and preserved in the collaborative chronologic record system tracking all the information for review and care methods. The general concept is that note keeping and messaging in a health record by the patient is likely to document poor side effects of a treatment plan more effectively and readily than a caregiver because they are the ones affected. This allows alterations and more accurate administration of treatment actions due to the communication.

Figure 3:
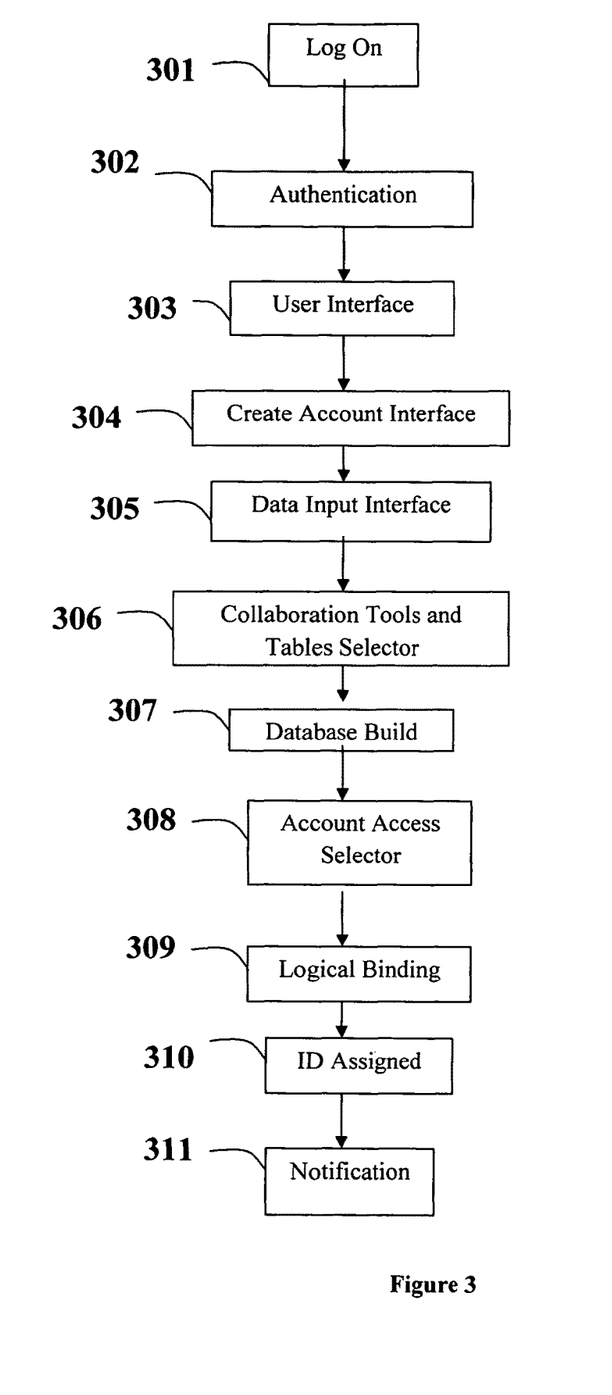
FIG. 3. Illustrates an example of the innovation workflow.

Referring now to FIG. 3, is a depiction of the workflow involved in creating a client account. The system presents the physician with a log on request 301. The user logs on to the system using a unique user ID. When a user logs in to the system a session ID is created 302. The session ID passes credentials (username & Password) via HTTP over SSL or TLS validating the user for the session. If authorized, the session ID acquires an authenticated token granting access to the database 302. The system recognizes the user by the unique ID and provides the user interface associated with that user ID 303. The user interface will present the folders, tools and tables that the user has permission to access, as determined by the user ID entered at log in. The user is then presented with the option to create an account 304. The system provides an interface 305 where the user can provide basic patient information such as name, address, contact information, email address and the like and an interface for selecting the collaboration tools 306 to be used for the patient. The system dynamically builds multiple database tables 307 reflecting the collaboration tools in the central record system based on the physician's selection. The system provides options to establish account access permissions to each collaborative tool and table 308 that have been selected. The system logically binds 309 the new account to that of the creating physician. The system assigns a unique user ID to the patient 310 for log on and provides notice 311 to patient via email, text or the like of the creation of the new account.

Figure 4:
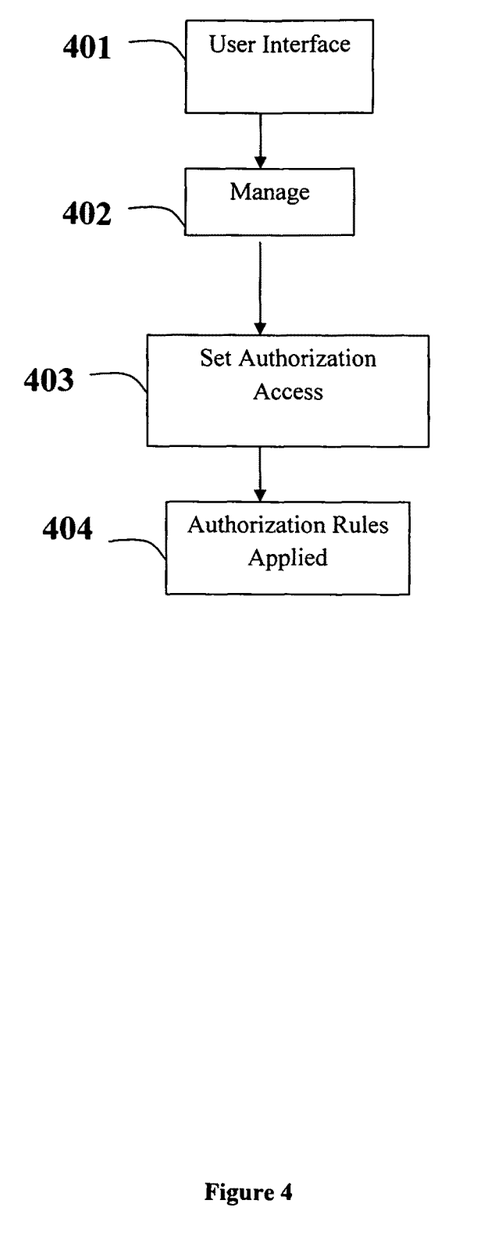
FIG. 4. Illustrates an example of the authorization process of the innovation.

Referring now to FIG. 4, details of the permission process is depicted. In this description it is understood that the innovation has a record authorization model built within the chronological record system as described elsewhere within this disclosure. Data owner 1 logs on to the system as described herein and is presented with the user interface 401 unique to the user's ID. Data owner 1 is presented with the option to manage 402 the user folders and tables as determined by the user unique ID. Data owner 1 sets permissions uniquely 403 for data owner 1's collaboration tools and tables with full access, no access, read, and write variables. The authorization process of item 402 and 403 establish the authorization rules to the database bindings of the collaboration record. 404 The authorization rules per collaboration table and can be changed only by the unique data owner. Additional data owners in the process of collaboration record binding control their unique authorization tables between other data owners.

Figure 5:
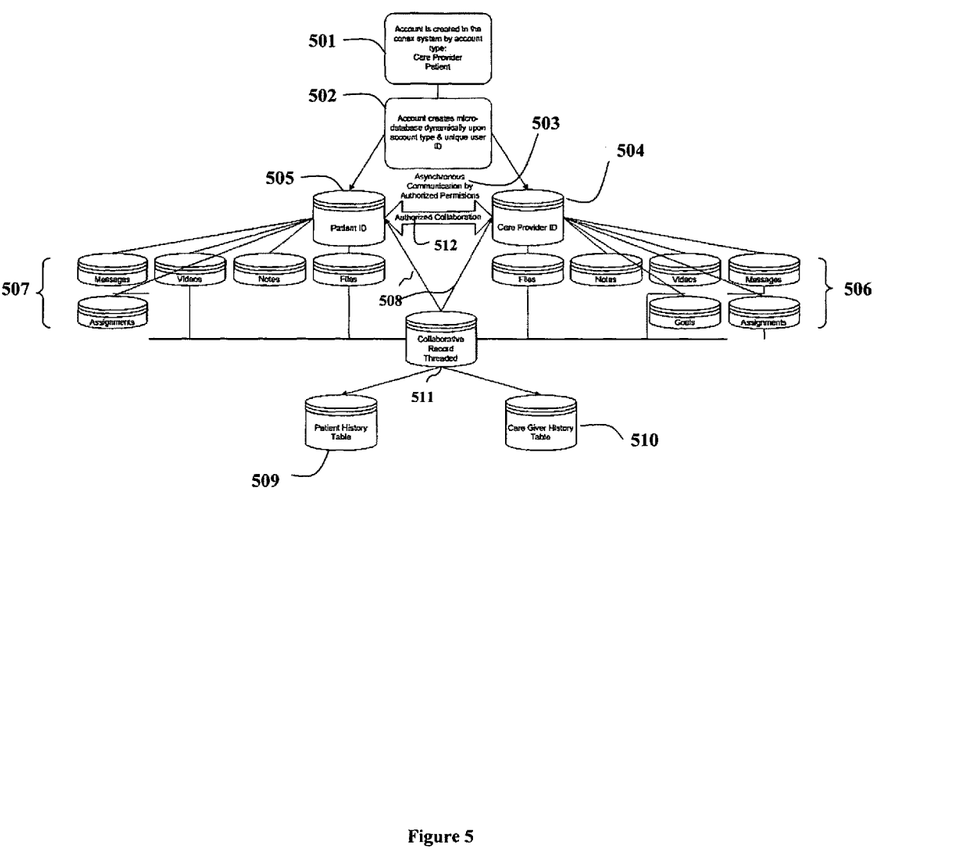
FIG. 5. Illustrates an example of the operational architecture of the innovation.

Referring to FIG. 5, an overview of the database operations are described. Following the hierarchy each user account created in the system is maintained in a users table. 501 When a user logs in to the system a session ID is created. The session ID passes credentials (username & Password) via HTTP over SSL or TLS validating the user for the session. If authorized, the session ID acquires an authenticated token granting access to the database and creates databases dynamically upon account type and unique user ID 502 and asynchronous communication is provided according to authorized permissions 503. The user's table 504, 505 creates a unique index table ID based upon the role chosen for the account (patient/provider). There are two index tables maintained in the database containing the unique ID's of the users table 504, 505. The first index table 504 contains the information associated with the provider account unique ID. The second index table 505 contains the information associated with the patient account unique ID. Each of the index tables 504, 505 are mapped to correlated tables 506, 507 associated to the role of the users table. The patient index table 505 with a patient unique ID is mapped to the various tools and tables 507 selected during the build and to which the patient is permitted access. The provider index table 504 with a provider unique ID is mapped to the various tools and tables 506 selected during the build and to which the provider is permitted access. Each of these tables 506, 507 stores and identifies data entries by unique ID. Table queries, table data entries, and table data removals are executed by unique ID (related index table), and sequence numbered per occurrence 508. The system contains a collaboration table 511 containing each unique user ID and authorization value per column for read, write, no access mapped to each data table associated to the unique user ID's role. The collaboration table 511 provides the joining function (threaded data sharing) 512 through authorization and sequencing (sequential data entries) between the patient and provider unique ID's and related data tables 504, 505. The collaboration table 511 is mapped to two history tables 509, 510. One history table 509 is maintained for entries associated with patient unique ID's. One history table 510 is maintained for entries associated with provider unique ID's. The history tables 509, 510 contain the journal entries of all activity correlated to the tables associated to the unique user ID.

The operational database system may be a SQL off the shelf product software. The system is designed to use a token based flow to the database that will drive decisions like encryption and specific market data sets. This process will guide the ability to use a powerful database engine while maintaining unique subset databases aligned to customer accounts.

Figure 6:
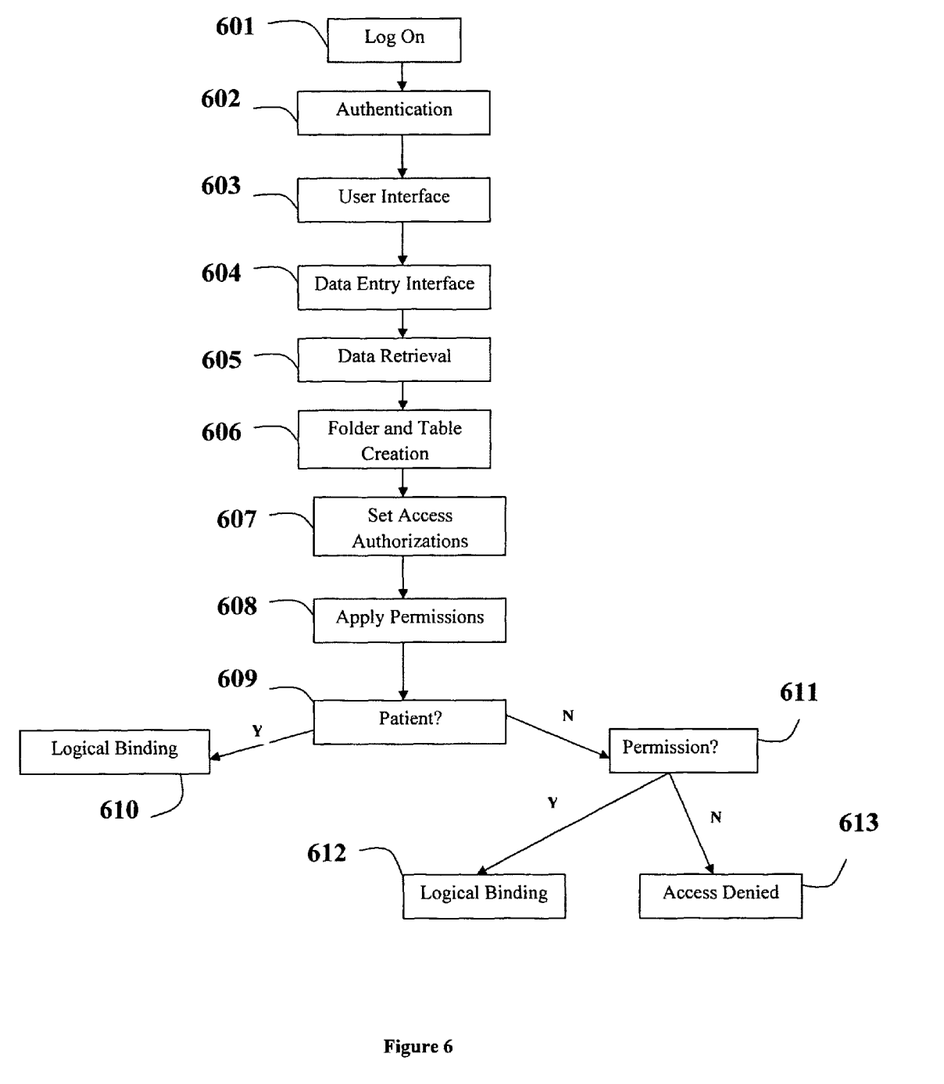
FIG. 6. Illustrates account sharing workflow process.

Referring now to FIG. 6 shows the creation and permissive account sharing aspect of the innovation through the user interface of the innovation. The system requests log on information 601 for the user and the user is authenticated 602 and presented with the user interface 603 as described herein. The user then navigates through the user interface to the option to manage the account and selects the option to create a shared folder/table. The system then provides a data entry interface for searching the system for a cooperating professional 604 and returns a list of the matching professionals 605 after the user input the search criteria. Search criteria can include, for example, first or last name, title, address, city, telephone, specialty or email. It should be recognized that other search criteria can be used as well. The user then selects the appropriate professional and the system creates a master folder for the professional selected 606. The system then presents the user with the folders available for the client and together with the options regarding sharing permissions including full access, read only, or no access 607 and applies those permissions to the appropriate folders 608. The system determines by user ID whether the user is a patient or a caregiver 609. If the user is a patient, the system logically binds the selected professional to the selected folders with the appropriate access as selected by the user 610 and the folder is marked as shared with appropriate permissions. 610 If the user is a caregiver, the system sends notification and a permission request 611 to the patient of the sharing request, the parameters of the request and a request for permission to allow access to the second caregiver. If the patient denies the request, the second caregiver is denied access 612. If the patient permits access, the system logically binds the selected professional to the selected folders with the appropriate access as permitted by the user 613 and the folder is marked as shared with appropriate permissions.

Figure 7:
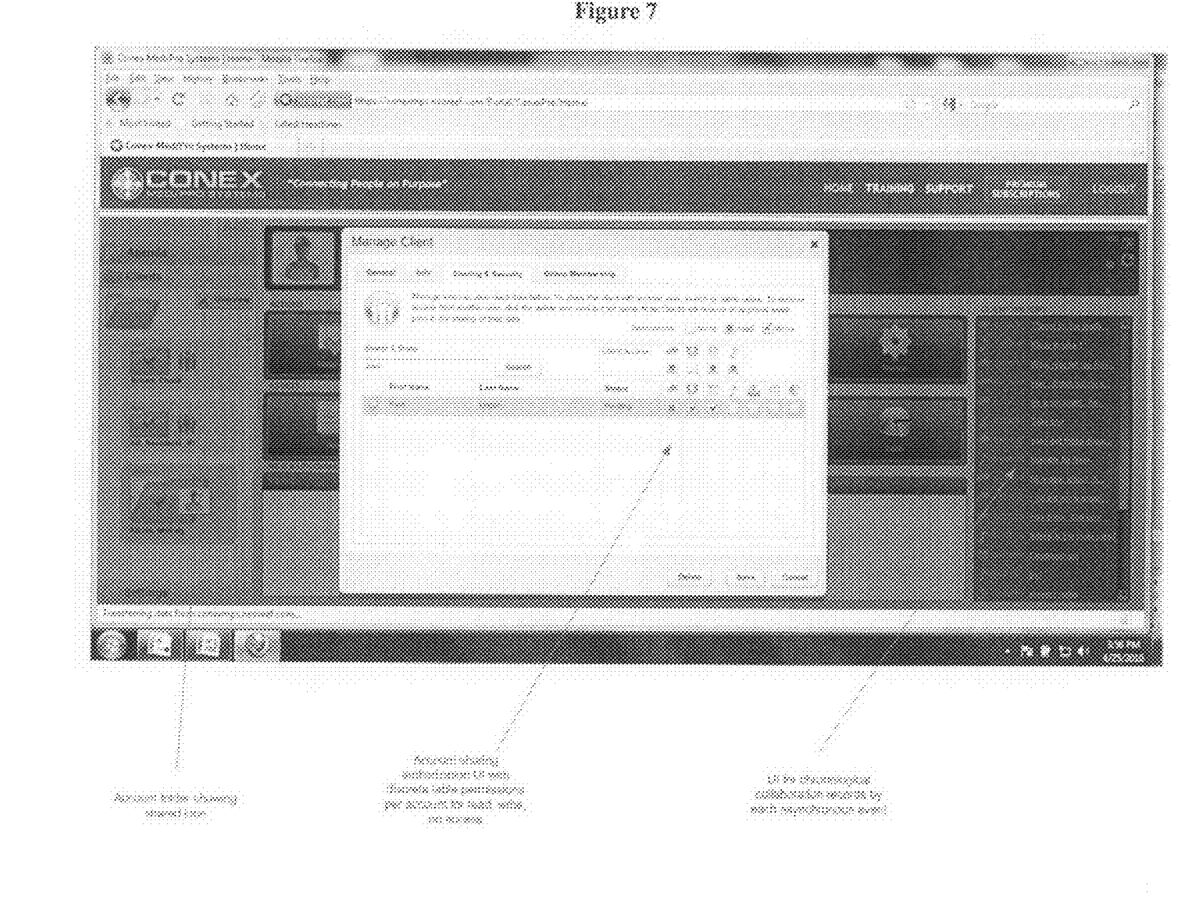
FIG. 7. Illustrates an example image view in accordance with aspects of the innovation.

Referring now to FIG. 7 shown is an example image of the user interface on the system. The user interface is the primary interface all customers will utilize within the system. In one embodiment, the entire user interface can be created using FLEX version 3 from Adobe. Ideally, the user interface includes visual icons for ease of use. Some of the visual effects contemplated include, but are not limited to, identifying folders by name and photo identification, visual display when actions are required on client folders. This allows visual recognition that actions have taken place requiring attention. The system may utilize simple visual icons that call up functions described by the icons or, like in many browser based applications, may navigate using browser based links, new windows and other browser functions. Ideally, however, the system does not require these typical browser functions and every function is actually executed on the application page itself for complete navigation and operational functions.

Figure 8:
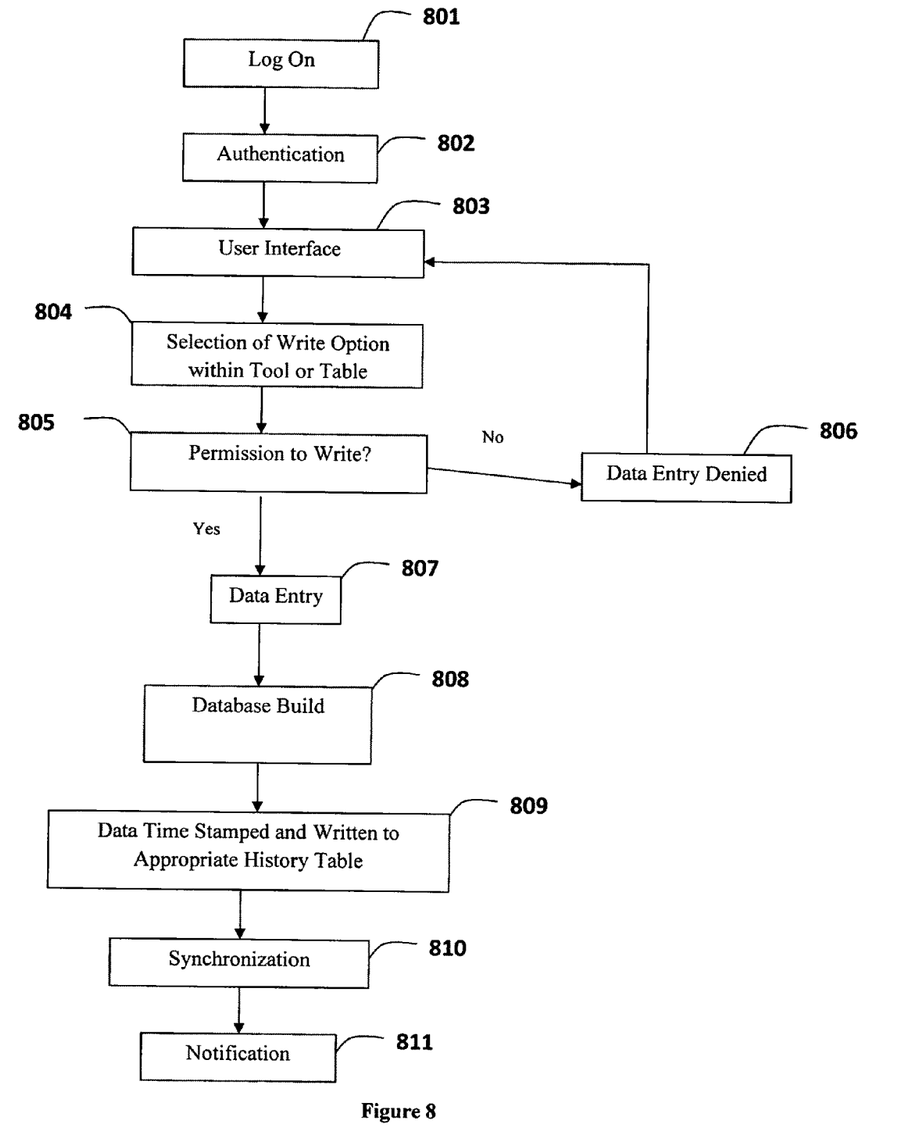
FIG. 8. Illustrates data entry workflow process.

Referring now to FIG. 8, depicted in workflow diagram 800 is the process of data entry into the innovative system. The system provides a log on request 801 to the user. After the user logs on using the user's unique system ID and the system identifies the user and authenticates the request 802, the system presents the user interface as previously described which includes the tools and tables that the user has permission to access 803. After the user selects a folder or table to modify 804, the system determines the access permissions for that particular user 805. If the user is not permitted to write in the selected folder, access is denied 806. If the user has permission to write to that table, the user is permitted to enter new data, information or the like into the table or folder 807. The user can also upload or download video or audio to the table. Once the user indicates that the data entry is complete, the system writes the data to the folder 808 and time stamps the data and writes it to the appropriate history table 809. The new data is then synchronized in the central folder and to the collaboration database 810. The system then provides notice via email, text or the like 811 to patient or physician that new data or information is present in the system.

What is described above includes examples of the innovation. Of course, it is not possible to describe each and every conceivable combination or embodiment of the innovation, but one of ordinary skill in the art may recognize that many further combinations, permutations or embodiments are possible. The invention is intended to embrace all such variations, modifications or alterations that fall within the scope of the claims.

What is claimed is:

1. A permissions-based collaborative patient and data management system for use in a clinical environment comprising:
   a chronological record database residing on at least one remote server, the chronological record database comprising:
      a patient-specific database comprising a plurality of patient-specific database tables, and wherein access to the patient-specific database is granted upon reception of either (a) a predetermined patient ID, or (b) a predetermined caregiver ID;
      a caregiver-specific database comprising a plurality of caregiver-specific database tables, wherein access to the caregiver-specific database is granted upon reception of a predetermined caregiver ID; and
      wherein at least one of the plurality of patient-specific database tables comprises a logical binding to at least one of the plurality of caregiver-specific database tables, and further wherein the logical binding is created upon creation of the at least one of the plurality of patient-specific database tables is built;
   the at least one remote server configured to be accessible by a user operated device capable of accessing the Internet through a web browser;
   the chronological record database configured to permit asynchronous recordkeeping;
   a user interface (UI) for accessing the chronological record database;
   a photograph application configured to (a) store photographs in the chronological record database, and (b) display photographs as a folder overlay in the UI;
   an audio application configured to (a) record audio, (b) store audio in the chronological record database, and (c) play back audio via the UI;
   a goal setting application configured to (a) present goals, (b) store goals in the chronological record database, (c) store awards associated with a predetermined goal, (d) calculate a progress towards completion of a predetermined goal based upon a predetermined formula, and (e) display a visual representation associated with a progress towards completion of a predetermined goal via the UI;
   a motivation application configured to (a) set and store milestone motivators to the chronological record database, and (b) present milestone motivators to patients as encouragement to reach goals stored in the goal setting application via the UI; and
   an assignment application configured to (a) store assignments to the chronological record database, (b) present assignments to patients via the UI, and (c) and track completion of assignments, wherein assignments comprise a choice-driven task comprising watching a video, reading a document, information, or sending a document.

2. The system of claim 1 further comprising a set of collaboration tools comprising:
   a calendaring application configured to (a) store appointment entries to the chronological record database, (b) display appointment entries via the UI, and (c) facilitate access to patient-specific database entries to caregivers;
   a notes application configured to (a) store notes to the chronological record database, and (b) display notes only to a predetermined caregiver ID via the UI;
   a messaging application configured to (a) transmit email like messages between a patient account and a caregiver account, and (b) store messages to the chronological record database; and
   a video application configured to (a) store links to videos to the chronological record database, (b) store text-based key points from associated videos, (c) store a due date and completion flag configured to track whether a patient has viewed an associated video, and (d) display videos via the UI.

3. The system of claim 2 further comprising an authorization process for setting permissions for accessing each collaboration tool.

4. The system of claim 3 further comprising a unique database for each data owner.

5. The system of claim 4 wherein one or more of the collaboration tools are logically bound to one or more unique databases.

6. The system of claim 5 further comprising at least one database associated with a unique user ID and one or more unique collaboration tables per user account.

7. The system of claim 6 further comprising at least one table that includes data that is tagged with identifying information.

8. The system of claim 7 further comprising a history table presented to the user.

9. The system of claim 1 wherein the chronological record database is an SQL database.

10. A method of managing patient data in a permissions-based collaborative patient and data management system for use in a clinical environment, the method comprising:
    receiving a log-in request via an Internet-connected device using a predetermined caregiver ID, the log-in request being received via secured transmission;
    verifying the caregiver ID in a chronological record database;
    transmitting data from the chronological record database upon verification of the caregiver ID, wherein the transmitted data is associated with the caregiver ID;
    receiving a request to create a patient-specific account;
    receiving patient specific information including patient (a) name, (b) address, (c) contact information, (d) email address, and (e) selected collaboration tools corresponding to applications that will be accessible to patients via a user interface (UI);
    building a patient-specific database corresponding to received patient specific information, the patient-specific database comprising a plurality of patient-specific tables;
    receiving account permission settings configured to restrict access to predetermined patient-specific tables;
    binding at least one of the plurality of patient-specific tables to the caregiver ID;
    assigning a patient ID to the patient-specific database, and transmitting the patient ID to the patient;
    receiving a request from the caregiver ID to enable access to the patient-specific database by a second caregiver ID;
    transmitting an authorization to the patient ID to allow the second caregiver ID to access the patient-specific database; and binding at least one of the plurality of patient-specific tables to the second caregiver ID.

11. An asynchronous permissions-based collaborative patient and data management system for use in a clinical environment, the system comprising:
- a chronological record database residing on at least one remote server, the chronological record database comprising:
  - a patient-specific database comprising a plurality of patient-specific database tables; and
  - a caregiver-specific database, and wherein the patient-specific database and the caregiver-specific database are asynchronously bound;
- the at least one remote server configured to be accessible by a user operated device capable of accessing the Internet through a web browser;
- a user interface (UI) for accessing the chronological record database;
- a goal setting application configured to (a) present goals, (b) store goals in the chronological record database, (c) store awards associated with a predetermined goal, (d) calculate a progress towards completion of a predetermined goal based upon a predetermined formula, and (e) display a visual representation associated with a progress towards completion of a predetermined goal via the UI;
- a motivation application configured to (a) set and store milestone motivators to the chronological record database, and (b) present milestone motivators to patients as encouragement to reach goals stored in the goal setting application via the UI; and
- an assignment application configured to (a) store assignments to the chronological record database, (b) present assignments to patients via the UI, and (c) and track completion of assignments, wherein assignments comprise a choice-driven task comprising watching a video, reading a document, information, or sending a document.

* * * * *

UNITED STATES PATENT AND TRADEMARK OFFICE
CERTIFICATE OF CORRECTION

PATENT NO.         : 8,756,250 B2
APPLICATION NO.    : 12/800676
DATED              : June 17, 2014
INVENTOR(S)        : Unger et al.

It is certified that error appears in the above-identified patent and that said Letters Patent is hereby corrected as shown below:

In the Claims

Column 9 Lines 13-65 Claim 1 should read

1. A permissions-based collaborative patient and data management system for use in a clinical environment comprising: a chronological record database residing on at least one remote server, the chronological record database comprising: a patient-specific database comprising a plurality of patient-specific database tables, and wherein access to the patient-specific database is granted upon reception of either (a) a predetermined patient ID, or (b) a predetermined caregiver ID; a caregiver-specific database comprising a plurality of caregiver-specific database tables, wherein access to the caregiver-specific database is granted upon reception of a predetermined caregiver ID; and wherein at least one of the plurality of patient-specific database tables comprises a logical binding to at least one of the plurality of caregiver-specific database tables, and further wherein the logical binding is created upon creation of the at least one of the plurality of patient-specific database tables is built; the at least one remote server configured to be accessible by a user operated device capable of accessing the Internet through a web browser; the chronological record database configured to permit asynchronous recordkeeping; a user interface (UI) for accessing the chronological record database; a photograph application configured to (a) store photographs in the chronological record database, and (b) display photographs as a folder overlay in the UI; an audio application configured to (a) record audio, (b) store audio in the chronological record database, and (c) play back audio via the UI; a goal setting application configured to (a) present goals, (b) store goals in the chronological record database, (c) store awards associated with a predetermined goal, (d) calculate a progress towards completion of a predetermined goal based upon a predetermined formula, and (e) display a visual representation associated with a progress towards completion of a predetermined goal via the UI; a motivation application configured to (a) set and store milestone motivators to the chronological record database, and (b) present milestone motivators to patients as encouragement to reach goals stored in the goal setting application via the UI; and an assignment application configured to (a) store assignments to the chronological record database, (b) present assignments to patients via the UI, and (c) and track completion of assignments, wherein assignments comprise a choice-driven task comprising watching a video, reading a document, getting information, or sending a document.

Signed and Sealed this
Twenty-third Day of September, 2014

Michelle K. Lee
*Deputy Director of the United States Patent and Trademark Office*

Column 11 and Column 12 lines 3-15 Claim 11 should read

11. An asynchronous permissions-based collaborative patient and data management system for use in a clinical environment, the system comprising:

a chronological record database residing on at least one remote server, the chronological record database comprising:

a patient-specific database comprising a plurality of patient-specific database tables; and a caregiver-specific database, and wherein the patient-specific database and the caregiver-specific database are asynchronously bound;

the at least one remote server configured to be accessible by a user operated device capable of accessing the Internet through a web browser;

a user interface (UI) for accessing the chronological record database;

a goal setting application configured to (a) present goals, (b) store goals in the chronological record database, (c) store awards associated with a predetermined goal, (d) calculate a progress towards completion of a predetermined goal based upon a predetermined formula, and (e) display a visual representation associated with a progress towards completion of a predetermined goal via the UI;

a motivation application configured to (a) set and store milestone motivators to the chronological record database, and (b) present milestone motivators to patients as encouragement to reach goals stored in the goal setting application via the UI; and an assignment application configured to (a) store assignments to the chronological record database, (b) present assignments to patients via the UI, and (c) and track completion of assignments, wherein assignments comprise a choice-driven task comprising watching a video, reading a document, getting information, or sending a document.